United States Patent
Henrywood

(10) Patent No.: US 12,220,197 B2
(45) Date of Patent: Feb. 11, 2025

(54) HAPTIC CONTROL OF A SURGEON CONSOLE

(71) Applicant: CMR SURGICAL LIMITED, Cambridge (GB)

(72) Inventor: Ross Hamilton Henrywood, Cambridge (GB)

(73) Assignee: CMR SURGICAL LIMITED, Cambridge (GB)

(*) Notice: Subject to any disclaimer, the term of this patent is extended or adjusted under 35 U.S.C. 154(b) by 858 days.

(21) Appl. No.: 17/285,609

(22) PCT Filed: Nov. 8, 2019

(86) PCT No.: PCT/GB2019/053155
§ 371 (c)(1),
(2) Date: Apr. 15, 2021

(87) PCT Pub. No.: WO2020/095053
PCT Pub. Date: May 14, 2020

(65) Prior Publication Data
US 2021/0315652 A1 Oct. 14, 2021

(30) Foreign Application Priority Data
Nov. 9, 2018 (GB) ...................... 1818320

(51) Int. Cl.
*A61B 34/00* (2016.01)
*A61B 5/1455* (2006.01)
(Continued)

(52) U.S. Cl.
CPC .......... *A61B 34/74* (2016.02); *A61B 5/14551* (2013.01); *A61B 34/35* (2016.02); *A61B 90/06* (2016.02); *A61B 2090/066* (2016.02)

(58) Field of Classification Search
CPC ......... A61B 34/74; A61B 34/35; A61B 34/00; A61B 90/06; A61B 90/00; A61B 5/14551; A61B 2090/066
See application file for complete search history.

(56) References Cited

U.S. PATENT DOCUMENTS 5,389,865 A    2/1995   Jacobus et al.
5,792,052 A * 8/1998   Isaacson .............. A61B 5/6826
                                                              600/323

(Continued)

FOREIGN PATENT DOCUMENTS

CN    101889900 A    11/2010
CN    102905641 A     1/2013
(Continued)

OTHER PUBLICATIONS

Chinese First Office Action from corresponding Chinese Application No. 201980072304.X dated Dec. 26, 2023.
(Continued)

*Primary Examiner* — Basil T. Jos
(74) *Attorney, Agent, or Firm* — Lando & Anastasi, LLP

(57) ABSTRACT

A surgical robotic system comprises a surgeon console, remote surgical robot, and a control unit. The surgeon console comprises a base connected to a hand controller by a linkage, the linkage comprising a plurality of joints whereby the configuration of the linkage can be altered. The surgeon console comprises a driver to drive each joint to move. The surgeon console further comprises a presence sensor to sense the presence of a surgeon's hand on the hand controller. The control unit receives user inputs from the hand controller, converts the received user inputs into command signals for driving manipulation of the surgical robot, receives sensory inputs from sensors including the presence sensor, and responds to, during a surgical operation, concurrently detecting from the received sensory inputs (i) the
(Continued)

lack of a surgeon's hand on the hand controller, and (ii) an external force additional to gravity acting on the hand controller, by controlling the drivers to drive the joints with a damped response in the direction of the external force.

18 Claims, 7 Drawing Sheets

(51) Int. Cl.
*A61B 34/35* (2016.01)
*A61B 90/00* (2016.01)

(56) References Cited

U.S. PATENT DOCUMENTS

| | | | |
|---|---|---|---|
| 8,332,072 | B1 | 12/2012 | Schaible et al. |
| 9,919,422 | B1* | 3/2018 | Horton ................. G05B 19/423 |
| 11,633,246 | B2* | 4/2023 | Cavalier ................ A61B 34/37 606/130 |
| 2010/0228264 | A1 | 9/2010 | Robinson et al. |
| 2015/0223897 | A1 | 8/2015 | Kostrzewski et al. |
| 2017/0252113 | A1 | 9/2017 | Beelen et al. |
| 2017/0325683 | A1* | 11/2017 | Larson ................... A61B 5/002 |
| 2018/0079090 | A1* | 3/2018 | Koenig ..................... G01L 3/14 |
| 2018/0214223 | A1 | 8/2018 | Turner |
| 2018/0361578 | A1* | 12/2018 | Muneto ................. B25J 9/1605 |
| 2019/0022857 | A1* | 1/2019 | Conus ................... B25J 9/0006 |

FOREIGN PATENT DOCUMENTS

| | | |
|---|---|---|
| CN | 104717936 A | 6/2015 |
| CN | 105101903 A | 11/2015 |
| CN | 106456260 A | 2/2017 |
| CN | 107028663 A | 8/2017 |
| CN | 107320186 A | 11/2017 |
| GB | 2575113 A | 1/2020 |
| JP | 1996150578 A | 6/1996 |
| JP | 2000084871 A | 3/2000 |
| JP | 2002139302 A | 5/2002 |
| JP | 2012071406 A | 4/2012 |
| JP | 2013034830 A | 2/2013 |
| JP | 2015516182 A | 6/2015 |
| JP | 2015519146 A | 7/2015 |
| JP | 2018506321 A | 3/2018 |
| WO | 2016112276 A1 | 7/2016 |
| WO | 2017169098 A1 | 10/2017 |
| WO | 2018112227 A2 | 6/2018 |

OTHER PUBLICATIONS

Japanese Notification of Reasons for Refusal from corresponding Japanese Patent Application No. 2021-517329 dated May 30, 2022.
Notification of Transmittal of the International Search Report and the Written Opinion of the International Searching Authority from corresponding PCT/GB2019/053155 dated Feb. 6, 2020.
United Kingdom Search Report from corresponding United Kingdom Application No. GB1818320.2 dated Apr. 18, 2019.
Chinese Second Office Action from corresponding Chinese Application No. 201980072304.X dated Aug. 15, 2024.

* cited by examiner

HAPTIC CONTROL OF A SURGEON CONSOLE

CROSS-REFERENCE TO RELATED APPLICATIONS

This application is a U.S. National Phase Application under 35 U.S.C. § 371 of International Application No. PCT/GB2019/053155, filed Nov. 8, 2019, which claims priority to United Kingdom Application No. 1818320.2, filed Nov. 9, 2018. Each application referenced above is hereby incorporated by reference in its entirety for all purposes.

BACKGROUND

This disclosure relates to controlling the motion of a surgical robot from a remote surgeon console.

FIG. 1 illustrates surgical robots 101, 102, 103 performing an operation on a person 104. Each robot comprises a base connected to a surgical instrument via a flexible arm. The robots are controlled remotely by a surgeon. The surgeon is located at a surgeon console 200, shown in FIG. 2. The surgeon manipulates hand controllers 201, 202. A control system converts the movement of the hand controllers into control signals to move the arm joints and/or instrument end effector of a surgical robot. A video feed from an endoscope at the surgical site is displayed on display 203 enabling the surgeon to view the instrument end effector that he is manipulating with the hand controllers 201, 202.

In order to reduce fatigue of the surgeon caused by supporting the hand controllers 201, 202, it is known to compensate each hand controller for gravity. In other words, the control system drives each joint of the linkage supporting the hand controller so as to provide a counteracting force to the gravity acting on that joint. If the surgeon lets go of the hand controller, the hand controller remains in the same position rather than dropping under gravity. Thus, the surgeon does not have to support the mass of the hand controller whilst manipulating it.

Gravity compensated hand controllers are light to handle and easy to manipulate. This is desirable, particularly for surgeons performing long operations. However, the hand controllers are vulnerable to being knocked, since the slightest contact will result in movement. This movement may then be replicated at the robot arm and/or instrument end effector.

It is known to use a so-called dead man's handle on the hand controller. This is a mechanical braking system, which brakes the system when the surgeon lets go of the hand controller.

Whilst effective, this additional braking system adds significant weight to the hand controller and supporting linkage, which is undesirable.

There is a need for a control system for controlling a surgeon's hand controller such that it is light and easy to handle by the surgeon during a surgical procedure whilst being less susceptible to being unintentionally moved.

SUMMARY OF THE INVENTION

According to a first aspect, there is provided a control unit for controlling a surgical robotic system, the surgical robotic system comprising a surgical robot remote from a surgeon console, the surgeon console comprising a base connected to a hand controller by a linkage, the linkage comprising a plurality of joints whereby the configuration of the linkage can be altered, for each joint the surgeon console comprising a driver configured to drive the joint to move, the surgeon console further comprising a presence sensor configured to sense the presence of a surgeon's hand on the hand controller, the control unit configured to: receive user inputs from the hand controller; convert the received user inputs into command signals for driving manipulation of the surgical robot; receive sensory inputs from sensors including the presence sensor; and respond to, during a surgical operation, concurrently detecting from the received sensory inputs (i) the lack of a surgeon's hand on the hand controller, and (ii) an external force additional to gravity acting on the hand controller, by controlling the drivers to drive the joints with a damped response in the direction of the external force.

The presence sensor may be a capacitive sensor, from which the control unit is configured to receive sensory inputs indicative of a detected capacitance.

The presence sensor may be an inductive sensor, from which the control unit is configured to receive sensory inputs indicative of a detected inductance.

The presence sensor may be a pulse oximeter, from which the control unit is configured to receive sensory inputs indicative of a detected oxygen saturation.

The presence sensor may be an optical sensor, from which the control unit is configured to receive sensory inputs indicative of a detected light signal or lack thereof.

The presence sensor may be configured to detect contact of the hand controller and the palm of the surgeon's hand or lack thereof.

The presence sensor may be a set of position sensors, each position sensor sensing the position of a joint of the linkage, from which the control unit is configured to receive a set of joint positions, the control unit being configured to determine the configuration of the linkage for that set of joint positions, and from subsequently received sets of joint positions determine motion of the linkage.

The control unit may detect the lack of a surgeon's hand on the hand controller if the determined motion of the linkage has a temporal profile of distance moved with a gradient greater than a threshold gradient.

The presence sensor may be a set of torque sensors, each torque sensor sensing the torque on a joint of the linkage, from which the control unit is configured to receive a set of joint torques.

The control unit may detect the lack of a surgeon's hand on the hand controller if the magnitude of a joint torque of the received set of joint torques exceeds a threshold value.

The surgeon console may comprise a set of position sensors, each position sensor sensing the position of a joint of the linkage, from which the control unit is configured to receive a set of joint positions, the control unit being configured to determine the configuration of the linkage for that set of joint positions, and from subsequently received sets of joint positions determine motion of the linkage.

The control unit may detect an external force additional to gravity acting on the hand controller if the determined motion of the linkage is non-zero.

The surgeon console may comprise a set of torque sensors, each torque sensor sensing the torque on a joint of the linkage, from which the control unit is configured to receive a set of joint torques.

The control unit may detect an external force additional to gravity acting on the hand controller if the magnitude of a joint torque of the received set of joint torques exceeds a baseline value.

The control unit may control the drivers to drive the joints so as to heavily damp motion in the direction of the external force.

The control unit may control the drivers to drive the joints so as to lightly damp motion in the direction of the external force.

The control unit may determine the gravitational torques on the joints in the linkage configuration indicated by the sensory inputs, and control the drivers to drive the joints so as to counteract the gravitational torques on the joints.

According to a second aspect, there is provided a surgeon console comprising: a base connected to a hand controller by a linkage, the linkage comprising a plurality of joints whereby the configuration of the linkage can be altered, for each joint the surgeon console comprising a driver configured to drive the joint to move; a presence sensor configured to sense the presence of a surgeon's hand on the hand controller; and the control unit of any of the above paragraphs.

According to a third aspect, there is provided a surgical robotic system comprising a surgeon console, a surgical robot remote from the surgeon console, and the control unit of any of the above paragraphs, the control unit being remote from the surgeon console.

According to a fourth aspect, there is provided a method of controlling motion of a hand controller of a surgeon console of a surgical robotic system, the surgical robotic system comprising a control unit and a surgical robot remote from the surgeon console, the surgeon console comprising a base connected to the hand controller by a linkage, the linkage comprising a plurality of joints whereby the configuration of the linkage can be altered, for each joint the surgeon console comprising a driver configured to drive the joint to move, the surgeon console further comprising a presence sensor configured to sense the presence of a surgeon's hand on the hand controller, the method comprising: receiving user inputs from the hand controller; converting the received user inputs into command signals for driving manipulation of the surgical robot; receiving sensory inputs from sensors including the presence sensor; and responding to, during a surgical operation, concurrently detecting from the received sensory inputs (i) the lack of a surgeon's hand on the hand controller, and (ii) an external force additional to gravity acting on the hand controller, by controlling the drivers to drive the joints with a damped response in the direction of the external force.

BRIEF DESCRIPTION OF THE DRAWINGS

The present disclosure will now be described by way of example with reference to the accompanying drawings. In the drawings.

DETAILED DESCRIPTION

The following description relates to a surgical robotic system comprising a surgical robot, a surgeon console and a control unit. A surgeon manipulates gravity compensated hand controllers of the surgeon console. The control unit converts this movement to command signals for driving corresponding manipulation of the remote surgical robot. The surgeon console comprises a presence sensor for sensing the presence of the surgeon's hand on the hand controller. This presence sensor relays its sensory data to the control unit. If the control unit detects that the surgeon's hand is not on the hand controller, and concurrently detects an external force acting on the hand controller (in addition to the gravitational forces), it controls the surgeon console to drive the hand controller with a damped response in the direction of the external force.

Figure 1:
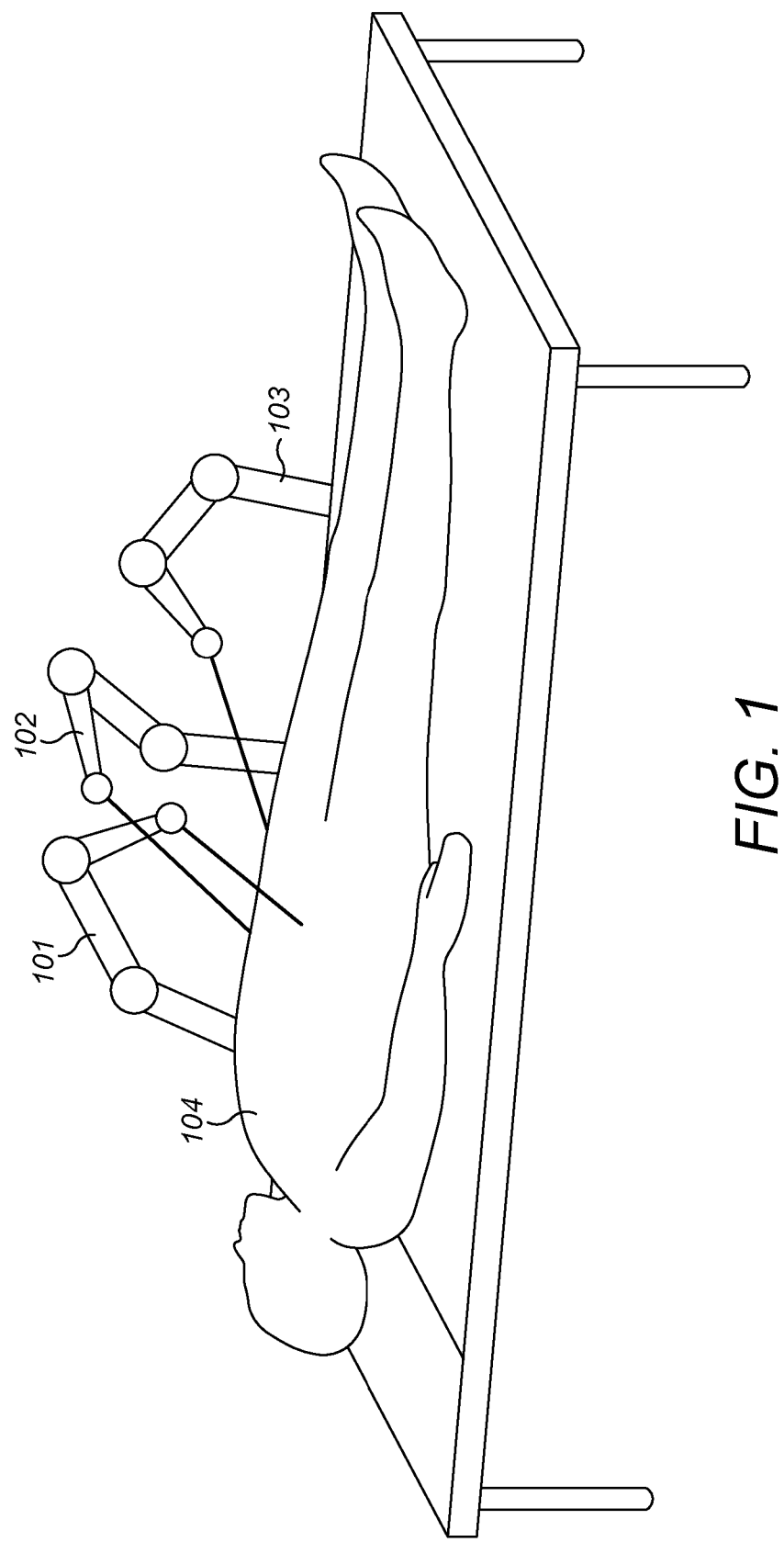
FIG. 1 illustrates a person being operated on by a set of surgical robots.
Figure 2:
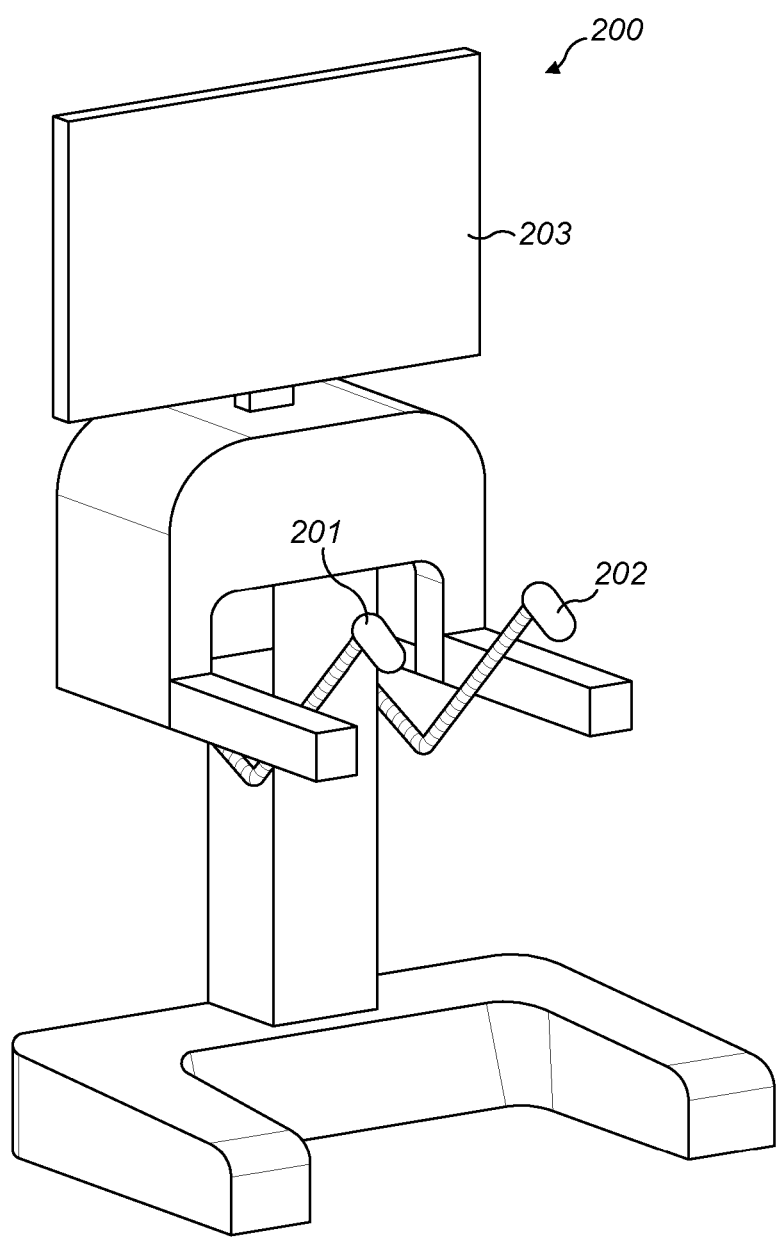
FIG. 2 illustrates a surgeon console.
Figure 3:
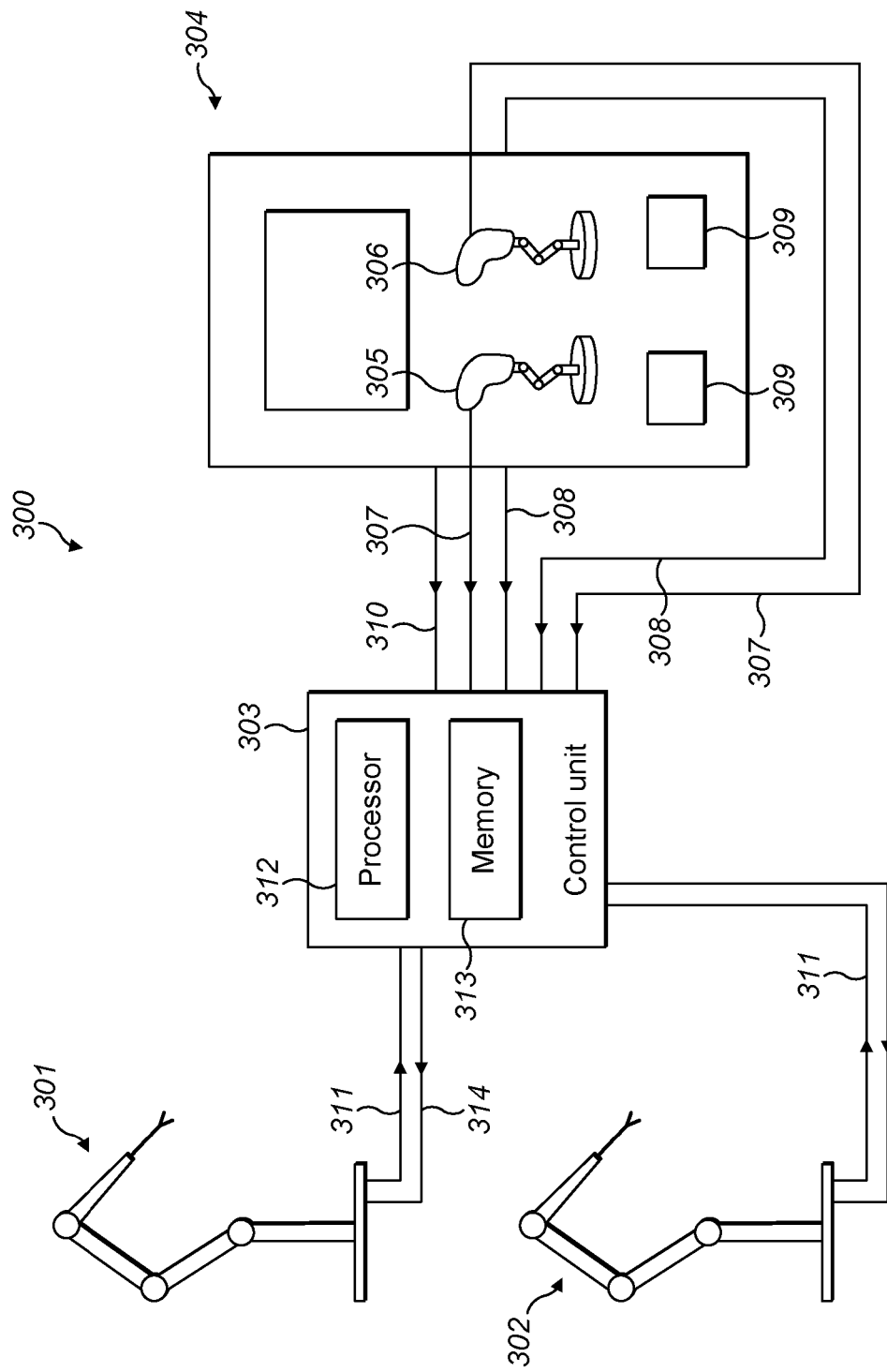
FIG. 3 illustrates a schematic diagram of a surgical robotic system.

FIG. 3 illustrates a surgical robotic system 300. The surgical robotic system 300 comprises two surgical robots 301, 302, a control unit 303, and a surgeon console 304. The surgeon console 304 comprises first and second hand controllers 305, 306. Each hand controller is connected to the base of the surgeon console by a flexible linkage. The control unit 303 receives user inputs 307 from the hand controllers. The control unit 303 also receives sensory inputs 308 from the surgeon console. The sensory inputs 308 are related to the hand controllers, and include sensory input from presence sensors 309. The sensory inputs may also include sensory data from position sensors and/or torque sensors sensing joints of the linkages connecting the hand controller to the base of the surgeon console. One or more of the position sensors and/or torque sensors may be located on the joints themselves. For example, a position/torque sensor may be located on the actuator of the joint it is sensing, that actuator being co-located with the joint. Alternatively, or in addition, one or more of the position sensors and/or torque sensors may be located remote from the joints. For example, a position/torque sensor may be located on the remote actuator of the joint it is sensing. An actuator which is remote from the joint it is driving may drive that joint by, for example, cable. The control unit may receive other inputs 310 from the surgeon console, such as foot pedal(s) inputs, button inputs, voice recognition inputs, gesture recognition inputs, eye recognition inputs etc. The control unit 303 may also receive inputs 311 from the surgical robots 301, 302. These inputs include sensory data from position sensors and torque sensors sensing the robot arm joints. The control unit 303 may receive other inputs 311 from each robot, such as force feedback, data from the surgical instrument etc. The control unit 303 drives the robots 301, 302 in response to the inputs it receives from the robots and the surgeon console. The control unit modulates the motion of the hand controllers 305, 306 in response to the inputs it receives from the surgeon console. The control unit 303 comprises a processor 312 and a memory 313. The memory stores, in a non-transient way, software code that can be executed by the processor to cause the processor to control the drivers in the manner described herein. Control unit 303 is shown as being remote from both the surgeon console and the surgical robots. Alternatively, the control unit 303 may be incorporated within the surgeon console 304. As a further alternative, the control unit 303 may be incorporated within any one of the surgical robots 301, 302.

Figure 4:
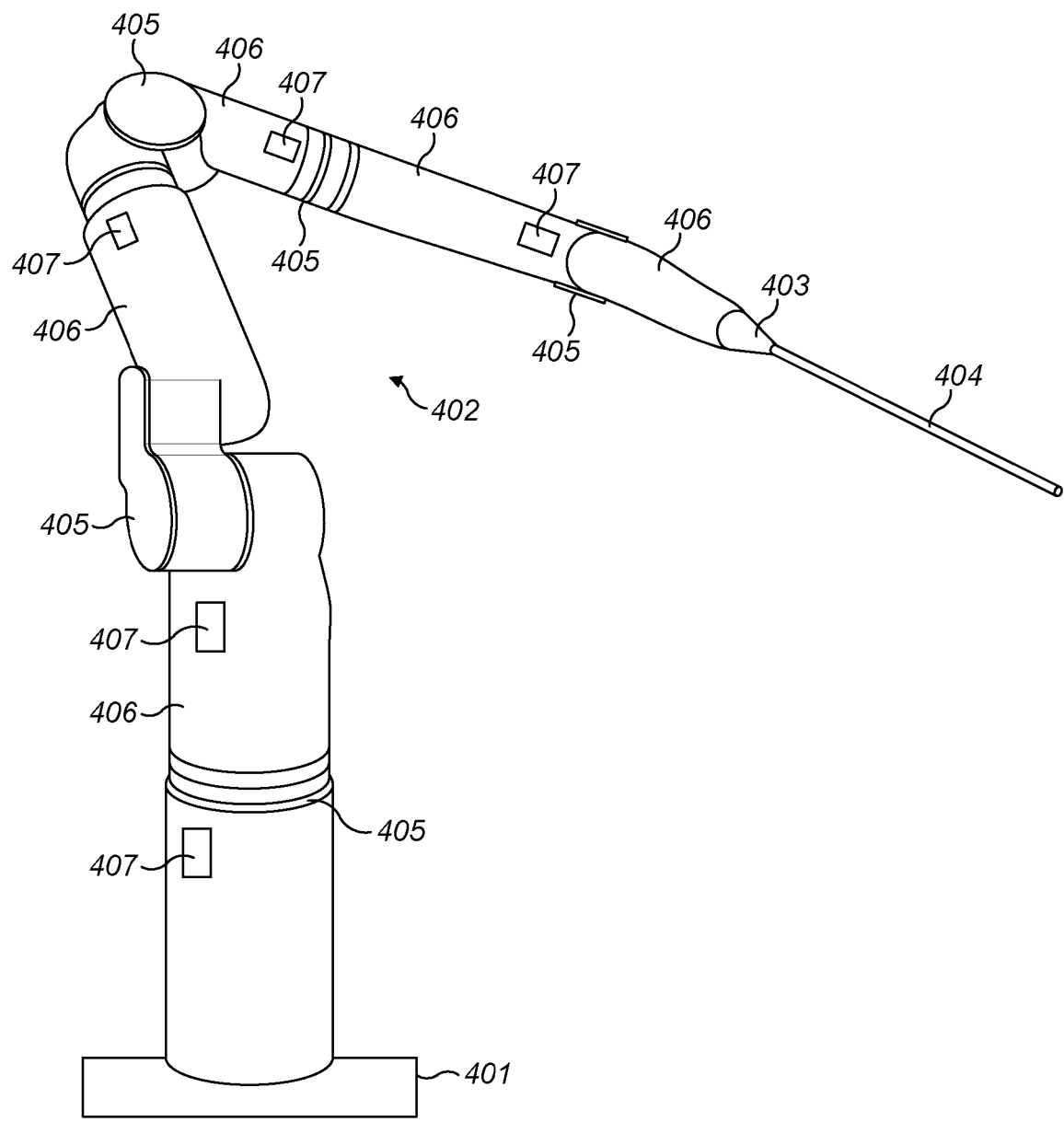
FIG. 4 illustrates a robot.

Each surgical robot 301, 302 is of the form illustrated in FIG. 4. The robot comprises a base 401. A flexible arm 402 extends from the base 401 of the robot to an attachment 403 for a surgical instrument 404. The arm 402 is articulated by means of multiple flexible joints 405 along its length. In between the joints are rigid arm members 406. The arm comprises a set of drivers, each driver 407 drives one or more joints 405.

Figure 5:
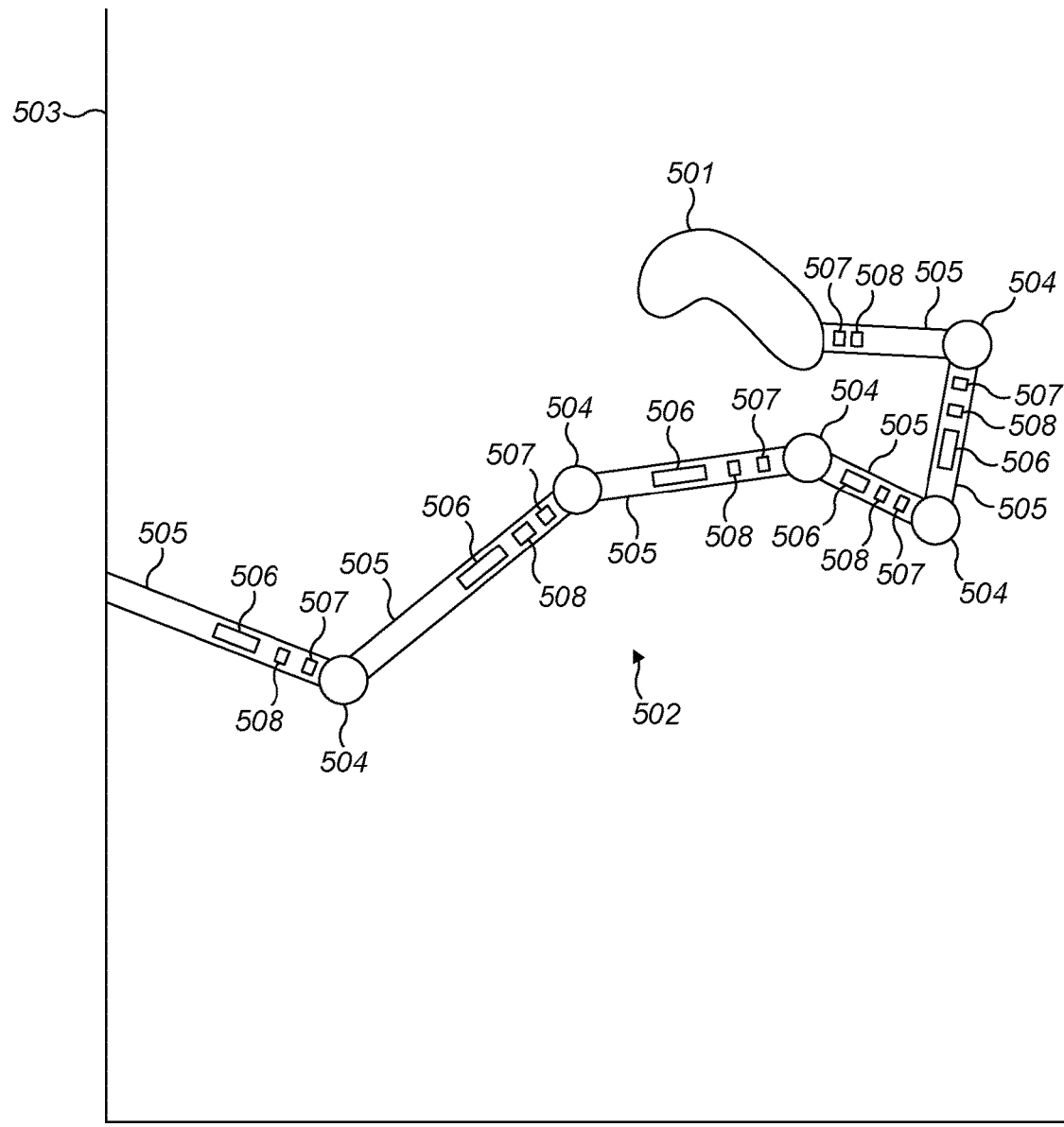
FIG. 5 illustrates a hand controller and linkage of a surgeon console.

FIG. 5 illustrates a hand controller of the surgeon console and its connection to the base of the surgeon console. The hand controller 501 is connected to the base of the surgeon console 503 by an articulated linkage 502. The linkage 502 is articulated by means of multiple flexible joints 504 along its length. In between the joints are rigid links 505. Thus, the configuration of the linkage 502 can be altered by manipulating the joints. The linkage comprises a set of drivers 506. Each driver 506 drives one or more joints 504.

The surgeon console comprises a series of sensors. These sensors comprise, for each joint, one or both of a position sensor 507 for sensing the position of the joint, and a torque sensor 508 for sensing the applied torque about the joint's rotation axis. One or both of the position and torque sensors for a joint may be integrated with the motor for that joint. The outputs of the sensors are passed to the control unit 303 where they form inputs to the processor 312.

The surgeon console comprises a presence sensor. The presence sensor is configured to sense the presence of the surgeon's hand on the hand controller. For example, the presence sensor may detect contact (or lack thereof) of the hand controller and the surgeon's palm. The presence sensor may be any one or more of the following:

1. A capacitive sensor. The capacitive sensor is located on the hand controller. The capacitive sensor is located on a portion of the surface of the hand controller that the surgeon contacts with his hand whilst manipulating the hand controller. The capacitive sensor sends sensory inputs to the control unit 303, those sensory inputs being indicative of a detected capacitance. The control unit 303 compares the detected capacitance to a threshold capacitance. If the detected capacitance is lower than the threshold capacitance, the control unit 303 determines that the surgeon's hand is on the hand controller. If the detected capacitance is higher than the threshold capacitance, the control unit 303 determines that the surgeon's hand is not on the hand controller.

2. An inductive sensor. The inductive sensor is located on the hand controller. The inductive sensor is located on a portion of the surface of the hand controller that the surgeon contacts with his hand whilst manipulating the hand controller. The inductive sensor sends sensory inputs to the control unit 303, those sensory inputs being indicative of a detected inductance. The control unit 303 compares the detected inductance to a threshold inductance. If the detected inductance is higher than the threshold inductance, the control unit 303 determines that the surgeon's hand is on the hand controller. If the detected inductance is lower than the threshold inductance, the control unit 303 determines that the surgeon's hand is not on the hand controller.

3. A pulse oximeter. The pulse oximeter is located on the hand controller. The pulse oximeter is located on a portion of the surface of the hand controller that the surgeon contacts with his hand whilst manipulating the hand controller. The pulse oximeter sends sensory inputs to the control unit 303, those sensory inputs being indicative of a detected oxygen saturation. The control unit 303 compares the detected oxygen saturation to a threshold oxygen saturation. If the detected oxygen saturation is higher than the threshold oxygen saturation, the control unit 303 determines that the surgeon's hand is on the hand controller. If the detected oxygen saturation is lower than the threshold oxygen saturation, the control unit 303 determines that the surgeon's hand is not on the hand controller.

4. An optical sensor. The optical sensor has a transmitter and a detector. The detector is located on the hand controller. The transmitter is located on the surgeon console within line of sight of the detector when the surgeon is not holding the hand controller in his hand. The transmitter is located on the surgeon console not within line of sight of the detector when the surgeon is holding the hand controller in his hand. The optical sensor sends sensory inputs to the control unit 303, those sensory inputs being indicative of a detected light signal. The control unit 303 compares the detected light level to a threshold light level. If the detected light level is lower than the threshold light level, the control unit 303 determines that the surgeon's hand is on the hand controller. If the detected light level is higher than the threshold light level, the control unit 303 determines that the surgeon's hand is not on the hand controller.

5. The joint position sensors on the linkage. Each position sensor senses the position of its associated joint. For example, it may sense the joint angle of the joint. The control unit receives the joint positions from the joint position sensors. The control unit has stored in the memory 313, the geometry/layout of the linkage. From the geometry of the linkage, and the received joint positions, the control unit 303 determines the current configuration of the linkage. From subsequent sets of received joint positions, the control unit determines subsequent configurations of the linkage. Thus, the control unit determines the motion of the linkage overtime. The control unit analyses the motion of the linkage in order to detect whether the surgeon's hand is on the hand controller. If the motion of the linkage is consistent with typical movement of the linkage caused by the surgeon moving the hand controller during a surgical procedure, then the control unit detects that the surgeon's hand is on the hand controller. If the motion of the linkage is not consistent with typical movement of the linkage caused by the surgeon moving the hand controller during a surgical procedure, then the control unit detects the lack of a surgeon's hand on the hand controller. For example, the control unit may assess the temporal profile of the distance moved by the linkage. If this profile has a gradient greater than a threshold gradient then the control unit may determine that the surgeon's hand is not on the hand controller.

6. The joint torque sensors on the linkage. Each torque sensor senses the torque of its associated joint. The control unit receives the joint torques from the joint torque sensors. If any individual joint torque exceeds a threshold value, the control unit may determine that the surgeon's hand is not on the hand controller. Alternatively, or additionally, the control unit may store the geometry/layout of the linkage in memory 313. From the geometry of the linkage and received sets of joint torques, the control unit 303 determines the motion of the linkage over time. The control unit analyses the motion of the linkage in order to detect whether the surgeon's hand is on the hand controller. If the motion of the linkage is consistent with typical movement of the linkage caused by the surgeon moving the hand controller during a surgical procedure, then the control unit detects that the surgeon's hand is on the hand controller. If the motion of the linkage is not consistent with typical movement of the linkage caused by the surgeon moving the hand controller during a surgical procedure, then the control unit detects the lack of a surgeon's hand on the hand controller. For example, the control unit may assess the temporal profile of the distance moved by the linkage. If this profile has a gradient greater than a threshold gradient then the control unit may determine that the surgeon's hand is not on the hand controller.

Figure 6:
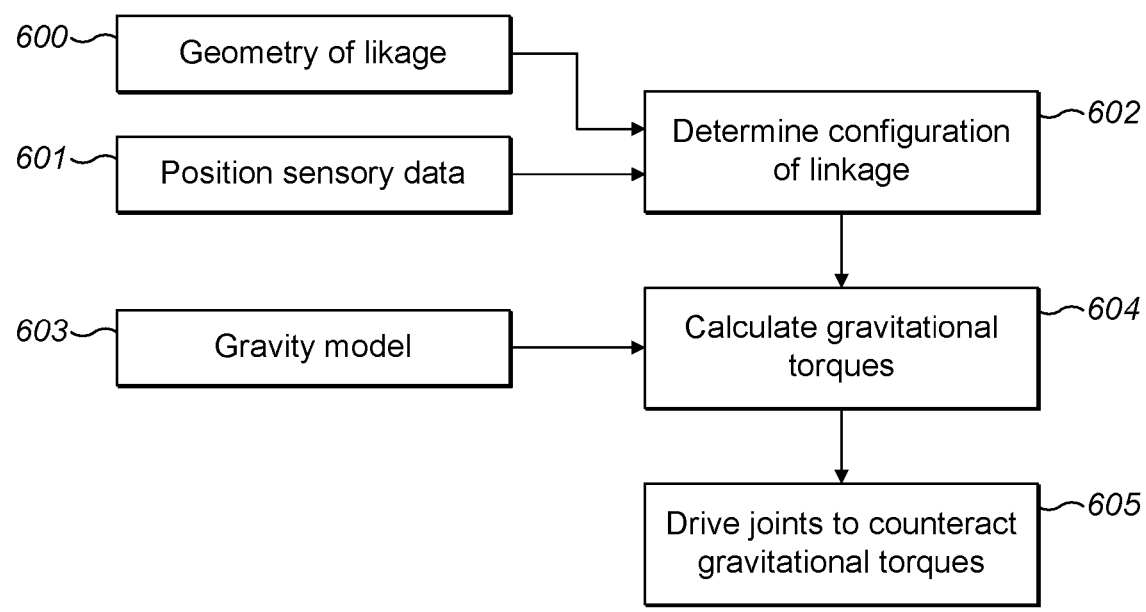
FIG. 6 is a flowchart showing the process of counteracting gravity on the hand controller and supporting linkage of a surgeon console.

The control unit drives the joints of the linkage connecting the hand controller to the base of the surgeon's console so as to counteract the gravitational torques on the joints. FIG. 6 illustrates steps implemented by the control unit 303 to do this.

The control unit receives as an input position sensory data 601 from the position sensors 507 sensing the joints of the linkage. For example, each position sensor may report the joint angle of the joint it is sensing. The control unit stores the geometry/layout of the linkage 502 in memory 313. The processor 312 of the control unit retrieves the stored geometry of the linkage from memory 313. At step 602, the processor 309 of the control unit determines the current configuration of the linkage from the received position sensory data and the geometry of the linkage. The configuration of the linkage is also known as the pose of the linkage. Suitably, the processor 312 stores the current configuration of the linkage in memory 313.

The control unit stores a gravity model 603 of the linkage in memory 313. The memory 313 stores for each element of the linkage and the attached hand controller, its mass, distance of its centre of mass from the preceding joint of the linkage, and the relationship between the centre of mass and the positional output of the joint sensor for the preceding joint. The processor 312 of the control unit retrieves the stored gravity model 603 from the memory 313. At step 604, the processor 312 of the control unit uses the current configuration of the linkage and the gravity model to model the effect of gravity on the elements of the linkage for the current configuration of the linkage. In doing this, the processor 312 determines the torque due to gravity acting on each joint of the linkage.

At step 605, the processor 312 controls the drivers 506 of the joints of the linkage to drive each joint 504 of the linkage so as to compensate for the gravitational torque acting on that joint calculated at step 604. In this way, the control unit maintains the position of the hand controller against gravity. Thus, the console supports the mass of the hand controller against gravity rather than the surgeon. If the surgeon lets go of the hand controller, it does not fall under gravity. Instead, it remains in its current position. This makes the hand controller light to use for the surgeon. Any force applied to the hand controller by the surgeon causes it to move.

It is not required for the control unit to actually determine the configuration of the linkage. The control unit may calculate the gravitational torques directly from the position sensory data, known geometry of the linkage, and gravity model.

The control unit performs the steps described in connection with FIG. 6 for each hand controller to which it is connected.

The control unit drives the joints of the robot arm in response to user inputs received from the hand controller(s) the surgeon is manipulating. The user inputs 307 from the hand controller(s) are received by the control unit 303. The control unit 303 converts the user inputs from the hand controller(s) to command signals for driving manipulation of the surgical robot. The control unit 303 then sends the command signals 314 to the drivers 407 of the surgical robot. The drivers 407 respond to the command signals 314 by driving their respective joints 405 in accordance with the command signals 314.

The following describes examples in which the control unit 303 utilises sensory data received from the surgeon console 304 to detect when a gravity compensated hand controller has been moved by a force other than that applied by a surgeon's hand during a surgical procedure. The control unit 303 responds by controlling the drivers of the linkage to drive the joints of the linkage so as to provide a resistive response in the direction of the external force. The force applied to each joint by the control system (excluding the force applied to counteract gravitational torque acting on the joint) is given by (a vector version of):

$$F(t) = m\ddot{x} + B\dot{x} + kx \quad \text{(equation 1)}$$

Where x is displacement, $\dot{x}$ is velocity, $\ddot{x}$ is acceleration, m is mass, B is the damping parameter, and k is the spring constant.

Since the control unit 303 controls the drivers to drive the joints of the linkage to apply the force of equation 1, the control unit may choose the values of m, B and k to provide the desired feel to the surgeon. For example, the control unit 300 may select any one of: a LIGHT mode in which m is small, such that the linkage and hand controller is light and hence not tiring for the surgeon to use; a HEAVY mode in which m is large, such that the linkage and hand controller is heavy and hence more easily controllable for the surgeon; a RESPONSIVE mode in which B is small, such that the hand controller is responsive to force applied by the surgeon's hand; a DAMPED mode in which B is large, such that motion of the hand controller is damped.

The spring constant may be small. k<1 N/mm. Suitably, the damping parameter B is sufficiently large to make the system controllable, but not so large that the system is hard to move. The damping parameter B is modified by the control unit in dependence on whether the surgeon's hand is on the hand controller. The damping parameter B may be set to B1 if the surgeon's hand is on the hand controller, and may be set to B2 if the surgeon's hand is not on the hand controller. The value of B1 is chosen such that the motion of the hand controller is light and responsive to force applied by the surgeon's hand. The value of B2 is chosen such that motion of the hand controller is heavily damped in response to force applied by an entity other than the surgeon's hand. Suitably, B2 is larger than B1. Preferably, B2>>B1.

Figure 7:
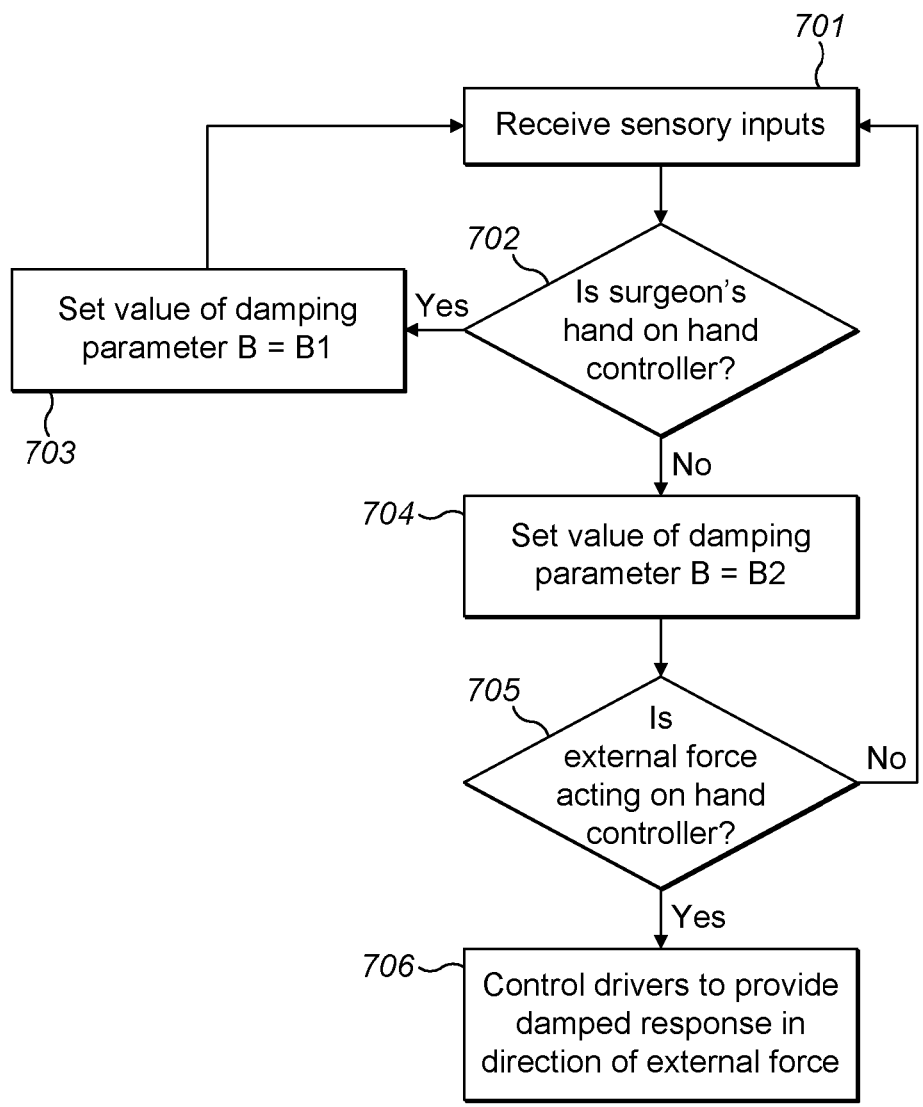
FIG. 7 is a flowchart showing the process of resisting motion of a hand controller.

With reference to FIG. 7, the control unit receives, at step 701, sensory inputs from the surgeon console. These sensory inputs include inputs from the presence sensor. The presence sensor may be any one or combination of the presence sensors described above.

At step 702, for each hand controller of the surgeon console, the control unit 303 determines whether the surgeon's hand is on the hand controller. The control unit analyses the sensory inputs from the presence sensor as described above in order to detect whether the surgeon's hand is on the hand controller or not. The control unit either detects that the surgeon's hand is on the hand controller, or detects the lack of a surgeon's hand on the hand controller. If the control unit determines that the surgeon's hand is on the hand controller, then the process continues to step 703. At step 703, the control unit sets the value of the damping parameter B to B1. The damping parameter B may already be set to B1 at step 702. In this case, the control unit retains the value of the damping parameter at B1. If, however, the damping parameter B is set to B2 at step 702, then the control unit changes the value of the damping parameter B to B1. The process then returns to step 701 where more sensory inputs are received from the presence sensor. If, at step 702, the control unit determines that the surgeon's hand is not on the hand controller, then the process continues to step 704.

At step 704, the control unit sets the value of the damping parameter B to B2. The damping parameter B may already be set to B2 at step 702. In this case, the control unit retains the value of the damping parameter B2. If, however, the damping parameter B is set to B1 at step 702, then the control unit changes the value of the damping parameter B to B2. The process then continues to step 705.

At step 705, the control unit assesses whether there is an external force acting on the hand controller. The control unit determines whether there is an external force acting on the hand controller using sensory data from either or both of position sensors and torques sensors sensing the joints 504 of linkage 502. As explained above, this external force is additional to the gravitational force acting on the hand controller.

In the case of position sensors, the control unit receives a set of joint positions of the linkage joints from the position sensors. From this and the stored geometry of the linkage, the control unit determines the configuration of the linkage for that set of joint positions. The control unit receives subsequent sets of joint positions at subsequent times. The control unit determines the configuration of the linkage at each of those subsequent times. The control unit thus determines the displacement of the linkage over time, i.e. the velocity of the linkage. The control unit determines that an external force additional to gravity is acting on the hand controller if the velocity of the linkage is non-zero after gravity has been accounted for. The control unit determines than no external force additional to gravity is acting on the hand controller if the velocity of the linkage is zero after gravity has been accounted for.

In the case of torque sensors, the control unit receives a set of joint torques of the linkage joints from the torque sensors. The control unit compares each of the joint torques to a baseline value. The control unit determines that an external force additional to gravity is acting on the hand controller if the magnitude of a joint torque exceeds the baseline value after gravity has been accounted for. The control unit determines that no external force additional to gravity is acting on the hand controller if there is no joint torque for which its magnitude exceeds the baseline value after gravity has been accounted for.

If, at step 705, the control unit determines that no external force additional to gravity is acting on the hand controller, the process returns to step 701 where more sensory inputs are received from the presence sensor. If the control unit determines that an external force additional to gravity is acting on the hand controller, then the process continues to step 706. At step 706, having determined that an external force additional to gravity is acting on the hand controller at the same time as the surgeon's hand is not on the hand controller, the control unit controls the drivers of the linkage to drive the linkage joints so as to provide a damped response in the direction of the external force. The control unit controls the drivers of the linkage to drive the linkage joints in accordance with a force given by a vector version of equation 1 above. In this equation x, $\dot{x}$, and $\ddot{x}$ are all derived from the position/torque sensory data. For example, in the case that sensory data from the position sensors is used: x is the displacement of the joints caused by the external force as measured by the joint position sensors; $\dot{x}$ is the first derivative of x calculated from the time history of x; and $\ddot{x}$ is the second derivative of x calculated from the time history of x. The sensory data may be filtered prior to being used in equation 1 to determine the force. For example, $\dot{x}$ may first be filtered at a low-pass filter to remove high-frequency control jitter. The values of m and k are set for the system as described above. The value of B is set to B2. The control unit then controls the drivers to apply a resistive torque to the joints of the linkage according to equation 1. Although the control unit causes the drivers to drive the linkage in the direction of the external force, that driven motion is heavily damped because of the coefficient B2 of the velocity component of the force.

The control unit may choose the value of B2 so as to provide any one of the following responses to the detection of the external force: a heavily damped motion in the direction of the external force, a lightly damped motion in the direction of the external force, or a wholly damped motion in the direction of the external force such that the hand controller is prevented from moving at all. The control unit may choose to provide a non-linear damping motion in the direction of the external force. This damping motion may be spring-like.

In the flowchart of FIG. 7, the control unit assesses whether the surgeon's hand is on the hand controller prior to assessing whether there is an external force additional to gravity acting on the hand controller. In one implementation, the control unit only assesses whether there is an external force additional to gravity acting on the hand controller when it has determined that the surgeon's hand is not on the hand controller. In another implementation, steps 702 and 705 are the other way around. Thus, the control unit assesses whether there is an external force additional to gravity acting on the hand controller prior to assessing whether the surgeon's hand is on the hand controller. Optionally, only when the control unit detects that there is an external force additional to gravity acting on the hand controller does it assess whether the surgeon's hand is on the hand controller. In another implementation, the control unit concurrently determines whether the surgeon's hand is on the hand controller and whether there is an external force additional to gravity acting on the hand controller. When the control unit detects both that the surgeon's hand is not on the hand controller and that an external force additional to gravity is acting on the hand controller, it controls the drivers to resist motion of the hand controller.

In the case that the presence sensor is implemented by a set of position sensors, those position sensors may provide both the sensory inputs for the presence sensor and the sensory inputs for determining whether an external force additional to gravity is acting on the hand controller.

In the case that the presence sensor is implemented by a set of torque sensors, those torque sensors may provide both the sensory inputs for the presence sensor and the sensory inputs for determining whether an external force additional to gravity is acting on the hand controller.

Compensating the hand controllers for gravity causes the hand controllers to be light and easy to manipulate by the surgeon. However, this also makes them vulnerable to being moved unintentionally. In prior art systems, this could cause the instrument end effector to move at the surgical site. It could also cause the hand controller to move to an undesirable position for the surgeon when the surgeon wishes to recommence control. The process described with respect to FIG. 7 detects unintentional motion of this nature and damps the response to it.

The process described with respect to FIG. 7 is intended for use during a surgical procedure. It is not intended for use whilst the surgeon has parked the hand controllers prior to a surgical procedure taking place or after a surgical procedure has taken place.

The position sensors could, for example, be potentiometers, optical position encoders, ultrasonic or radio distance sensors. The torque sensors could, for example, be resistance-based strain gauges, piezoelectric strain gauges or semiconductor strain gauges. The drivers for driving the joints of the linkage to move could be rotary or linear motors, or means other than motors: for example hydraulic or pneumatic rams.

The robot could be used for purposes other than surgery. For example, the robot could be used in car manufacturing for viewing the inside of an engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A control unit configured to control a surgical robotic system, the surgical robotic system comprising a surgical robot remote from a surgeon console, the surgeon console comprising a base connected to a hand controller by a linkage, the linkage comprising a plurality of joints whereby the configuration of the linkage can be altered, for each joint the surgeon console comprising a driver configured to drive the joint to move, the surgeon console further comprising a presence sensor configured to sense the presence of a surgeon's hand on the hand controller, the control unit configured to:
receive user inputs from the hand controller;
convert the received user inputs into command signals configured to drive manipulation of the surgical robot;
receive sensory inputs from sensors including the presence sensor; and
respond to, during a surgical operation, concurrently detecting from the received sensory inputs (i) the lack of a surgeon's hand on the hand controller, and (ii) an external force additional to gravity acting on the hand controller, by controlling the drivers to drive the joints with a damped response in the direction of the external force.

2. The control unit as claimed in claim 1, wherein the presence sensor is a capacitive sensor, from which the control unit is configured to receive sensory inputs indicative of a detected capacitance.

3. The control unit as claimed in claim 1, wherein the presence sensor is an inductive sensor, from which the control unit is configured to receive sensory inputs indicative of a detected inductance.

4. The control unit as claimed in claim 1, wherein the presence sensor is a pulse oximeter, from which the control unit is configured to receive sensory inputs indicative of a detected oxygen saturation.

5. The control unit as claimed in claim 1, wherein the presence sensor is an optical sensor, from which the control unit is configured to receive sensory inputs indicative of a detected light signal or lack thereof.

6. The control unit as claimed in claim 1, wherein the presence sensor is configured to detect contact of the hand controller and the palm of the surgeon's hand or lack thereof.

7. The control unit as claimed in claim 1, wherein the presence sensor is a set of position sensors, each position sensor sensing the position of a joint of the linkage, from which the control unit is configured to receive a set of joint positions, the control unit being configured to determine the configuration of the linkage for that set of joint positions, and from subsequently received sets of joint positions determine motion of the linkage.

8. The control unit as claimed in claim 7, configured to detect the lack of a surgeon's hand on the hand controller if the determined motion of the linkage has a temporal profile of distance moved with a gradient greater than a threshold gradient.

9. The control unit as claimed in claim 1, wherein the presence sensor is a set of torque sensors, each torque sensor sensing the torque on a joint of the linkage, from which the control unit is configured to receive a set of joint torques.

10. The control unit as claimed in claim 9, configured to detect the lack of a surgeon's hand on the hand controller if the magnitude of a joint torque of the received set of joint torques exceeds a threshold value.

11. The control unit as claimed in claim 1, wherein the surgeon console comprises a set of position sensors, each position sensor sensing the position of a joint of the linkage, from which the control unit is configured to receive a set of joint positions, the control unit being configured to determine the configuration of the linkage for that set of joint positions, and from subsequently received sets of joint positions determine motion of the linkage.

12. The control unit as claimed in claim 11, configured to detect an external force additional to gravity acting on the hand controller if the determined motion of the linkage is non-zero.

13. The control unit as claimed in claim 1, wherein the surgeon console comprises a set of torque sensors, each torque sensor sensing the torque on a joint of the linkage, from which the control unit is configured to receive a set of joint torques.

14. The control unit as claimed in claim 13, configured to detect an external force additional to gravity acting on the hand controller if the magnitude of a joint torque of the received set of joint torques exceeds a baseline value.

15. The control unit as claimed in claim 1, configured to:
determine the gravitational torques on the joints in the linkage configuration indicated by the sensory inputs, and
control the drivers to drive the joints so as to counteract the gravitational torques on the joints.

16. A surgeon console comprising:
a base connected to a hand controller by a linkage, the linkage comprising a plurality of joints whereby the configuration of the linkage can be altered, for each joint the surgeon console comprising a driver configured to drive the joint to move;
a presence sensor configured to sense the presence of a surgeon's hand on the hand controller; and
the control unit of claim 1.

17. A surgical robotic system comprising a surgeon console, a surgical robot remote from the surgeon console, and the control unit of claim 1, the control unit being remote from the surgeon console.

18. A method of controlling motion of a hand controller of a surgeon console of a surgical robotic system, the surgical robotic system comprising a control unit and a surgical robot remote from the surgeon console, the surgeon console comprising a base connected to the hand controller by a linkage, the linkage comprising a plurality of joints whereby the configuration of the linkage can be altered, for each joint the surgeon console comprising a driver configured to drive the joint to move, the surgeon console further comprising a presence sensor configured to sense the presence of a surgeon's hand on the hand controller, the method comprising:
- receiving user inputs from the hand controller;
- converting the received user inputs into command signals configured to drive manipulation of the surgical robot;
- receiving sensory inputs from sensors including the presence sensor; and
- responding to, during a surgical operation, concurrently detecting from the received sensory inputs (i) the lack of a surgeon's hand on the hand controller, and (ii) an external force additional to gravity acting on the hand controller, by controlling the drivers to drive the joints with a damped response in the direction of the external force.

* * * * *